United States Patent
Greenwald et al.

(10) Patent No.: US 10,952,671 B2
(45) Date of Patent: *Mar. 23, 2021

(54) SYSTEM FOR MONITORING A PHYSIOLOGICAL PARAMETER OF PLAYERS ENGAGED IN A SPORTING ACTIVITY

(71) Applicant: Riddell, Inc., Des Plaines, IL (US)

(72) Inventors: Richard M. Greenwald, Norwich, VT (US); Jeffrey J. Chu, Quechee, VT (US); Joseph J. Crisco, Barrington, RI (US); Thad M. Ide, Chicago, IL (US)

(73) Assignee: Riddell, Inc., Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/417,134

(22) Filed: May 20, 2019

(65) Prior Publication Data

US 2019/0290201 A1     Sep. 26, 2019

Related U.S. Application Data

(63) Continuation of application No. 14/450,928, filed on Aug. 4, 2014, now Pat. No. 10,292,650, which is a (Continued)

(51) Int. Cl.
*A61B 5/00* (2006.01)
*A61B 5/11* (2006.01)
(Continued)

(52) U.S. Cl.
CPC ............ *A61B 5/6803* (2013.01); *A42B 3/046* (2013.01); *A61B 5/002* (2013.01); *A61B 5/0002* (2013.01);
(Continued)

(58) Field of Classification Search
CPC ................ A61B 5/6803; A61B 5/0002; A61B 2562/0219
See application file for complete search history.

(56) References Cited

U.S. PATENT DOCUMENTS

| 3,646,606 A | 2/1972 | Buxton |
| 3,845,389 A | 10/1974 | Phillips |

(Continued)

FOREIGN PATENT DOCUMENTS

| DE | 19707495 | 8/1998 |
| EP | 0315498 | 5/1989 |

(Continued)

OTHER PUBLICATIONS

Murray, C., Smart Helmets Monitor Football Injuries, Dec. 18, 2003, Embedded.com, 3 pp. (Year: 2003).*

(Continued)

*Primary Examiner* — Toan M Le
(74) *Attorney, Agent, or Firm* — Barnes & Thornburg LLP (57) ABSTRACT

The present invention provides a system for monitoring a physiological parameter of players engaged in a sporting activity. The system includes a plurality of reporting units, a controller, and a signaling device. The reporting unit has an arrangement of sensing devices that measure the physiological parameter of an individual player and generate parameter data. The controller receives the parameter data transmitted from each reporting unit and then processes the parameter data to calculate a parameter result. When the parameter result exceeds a predetermined value, the controller communicates with a signaling device that provides an alert to sideline personnel to monitor the player(s) in question. The system also includes a remote storage device for holding historical data collected by the system which permits subsequent analysis. The system can monitor a (Continued)

number of player physiological parameters, including the acceleration of a player's body part that experiences an impact and the temperature of each player.

22 Claims, 4 Drawing Sheets

Related U.S. Application Data continuation of application No. 11/225,880, filed on Sep. 13, 2005, now Pat. No. 8,797,165.

(60) Provisional application No. 60/609,555, filed on Sep. 13, 2004.

(51) Int. Cl.
*A63B 71/06* (2006.01)
*A42B 3/04* (2006.01)
*A63B 71/10* (2006.01)
*A63B 102/14* (2015.01)
*A61B 5/01* (2006.01)
*A63B 102/22* (2015.01)

(52) U.S. Cl.
CPC .............. *A61B 5/11* (2013.01); *A61B 5/1122* (2013.01); *A61B 5/4064* (2013.01); *A61B 5/4076* (2013.01); *A61B 5/6814* (2013.01); *A61B 5/7282* (2013.01); *A61B 5/746* (2013.01); *A63B 71/06* (2013.01); *A63B 71/10* (2013.01); *A61B 5/01* (2013.01); *A61B 2503/10* (2013.01); *A61B 2562/0219* (2013.01); *A63B 2102/14* (2015.10); *A63B 2102/22* (2015.10); *A63B 2208/12* (2013.01); *A63B 2220/40* (2013.01); *A63B 2225/30* (2013.01); *A63B 2230/06* (2013.01); *A63B 2230/50* (2013.01); *A63B 2230/60* (2013.01); *A63B 2243/007* (2013.01)

(56) References Cited

U.S. PATENT DOCUMENTS

| | | |
|---|---|---|
| 3,902,478 A | 9/1975 | Konopasek |
| 3,972,038 A | 7/1976 | Fletcher |
| 3,972,320 A | 8/1976 | Kalman |
| 4,196,429 A | 4/1980 | Davis |
| 4,250,894 A | 2/1981 | Frei |
| 4,440,160 A | 4/1984 | Fischell |
| 4,468,656 A | 8/1984 | Clifford |
| 4,502,035 A | 2/1985 | Obenauf |
| 4,590,801 A | 5/1986 | Merhav |
| 4,608,998 A | 9/1986 | Murdock |
| 4,665,748 A | 5/1987 | Peters |
| 4,691,556 A | 9/1987 | Mellander |
| 4,761,005 A | 8/1988 | French |
| 4,763,275 A | 8/1988 | Carlin |
| 4,763,284 A | 8/1988 | Carlin |
| 4,873,867 A | 10/1989 | McPherson |
| 4,883,271 A | 11/1989 | French |
| 4,982,452 A | 1/1991 | Chaise |
| 4,996,877 A | 3/1991 | Stewart |
| 5,203,034 A | 4/1993 | Foehl |
| 5,221,088 A | 6/1993 | McTeigue |
| 5,287,562 A | 2/1994 | Rush |
| 5,327,588 A | 7/1994 | Garneau |
| 5,331,969 A | 7/1994 | Silberstein |
| 5,348,008 A | 9/1994 | Bornn |
| 5,383,363 A | 1/1995 | Kulmaczewski |
| 5,408,879 A | 4/1995 | Vreeburg |
| 5,473,527 A | 12/1995 | Gold |
| 5,487,305 A | 1/1996 | Ristic |
| 5,539,935 A | 7/1996 | Rush, III |
| 5,546,609 A | 8/1996 | Rush, III |
| 5,596,491 A | 1/1997 | Gold |
| 5,615,132 A | 3/1997 | Horton |
| 5,621,922 A | 4/1997 | Rush, III |
| 5,645,077 A | 7/1997 | Foxlin |
| 5,697,099 A | 12/1997 | Siska, Jr. |
| 5,704,707 A | 1/1998 | Gebelein |
| 5,723,786 A | 3/1998 | Klapman |
| 5,745,028 A | 4/1998 | Hock |
| 5,745,029 A | 4/1998 | Garcia |
| 5,819,206 A | 10/1998 | Horton |
| 5,856,811 A | 1/1999 | Shih |
| 5,896,590 A | 4/1999 | Fleisch |
| 5,916,181 A | 6/1999 | Socci |
| 5,978,972 A | 11/1999 | Stewart |
| 6,002,994 A | 12/1999 | Lane |
| 6,009,563 A | 1/2000 | Swanson |
| 6,032,530 A | 3/2000 | Hock |
| 6,056,674 A | 5/2000 | Cook |
| 6,057,758 A | 5/2000 | Dempsey |
| 6,090,044 A | 7/2000 | Bishop |
| 6,186,145 B1 | 2/2001 | Brown |
| 6,198,394 B1 | 3/2001 | Jacobsen |
| 6,204,813 B1 | 3/2001 | Wadell |
| 6,259,944 B1 | 7/2001 | Margulis |
| 6,298,483 B1 | 10/2001 | Schiebl |
| 6,301,718 B1 | 10/2001 | Rigal |
| 6,302,844 B1 | 10/2001 | Walker |
| 6,331,168 B1 | 12/2001 | Socci |
| 6,361,507 B1 | 3/2002 | Foxlin |
| 6,366,871 B1 | 4/2002 | Geva |
| 6,375,612 B1 | 4/2002 | Guichon |
| 6,397,151 B1 | 5/2002 | Yamagishi |
| 6,406,168 B1 | 6/2002 | Whiting |
| 6,441,747 B1 | 8/2002 | Khair |
| 6,484,133 B1 | 11/2002 | Vogt |
| 6,539,336 B1 | 3/2003 | Vock |
| 6,567,116 B1 | 5/2003 | Aman |
| 6,588,022 B1 | 7/2003 | Anders |
| 6,611,782 B1 | 8/2003 | Wooster |
| 6,611,789 B1 | 8/2003 | Darley |
| 6,647,787 B2 | 11/2003 | Fore |
| 6,730,047 B2 | 5/2004 | Socci |
| 6,735,551 B2 | 5/2004 | Voegeli |
| 6,748,250 B1 | 6/2004 | Berman |
| 6,798,392 B2 | 9/2004 | Hartwell |
| 6,826,509 B2 * | 11/2004 | Crisco, III ............. A42B 3/046 |
| | | 702/141 |
| 6,925,851 B2 | 8/2005 | Reinbold |
| 6,964,638 B2 | 11/2005 | Theodoracopulos |
| 7,054,784 B2 | 5/2006 | Flentov |
| 7,087,015 B1 | 8/2006 | Comrie |
| 7,092,846 B2 | 8/2006 | Vock |
| 7,162,392 B2 | 1/2007 | Vock |
| 7,386,401 B2 | 6/2008 | Vock |
| 7,478,108 B2 | 1/2009 | Townsend |
| 7,526,389 B2 * | 4/2009 | Greenwald ............. A42B 3/046 |
| | | 2/425 |
| 7,548,168 B2 | 6/2009 | Ishikawa |
| 7,693,668 B2 | 4/2010 | Vock |
| 8,280,681 B2 | 10/2012 | Vock |
| 8,382,685 B2 | 2/2013 | Vaccari |
| 8,468,613 B2 | 6/2013 | Harty |
| 8,690,655 B2 | 4/2014 | Meyer |
| 8,786,415 B2 | 7/2014 | Cavallaro |
| 8,797,165 B2 * | 8/2014 | Greenwald .......... A61B 5/0002 |
| | | 340/573.1 |
| 8,860,570 B2 | 10/2014 | Thomas |
| 9,141,759 B2 | 9/2015 | Burich |
| 9,554,607 B2 | 1/2017 | Mack |
| 9,566,471 B2 | 2/2017 | Deangelis |
| 9,900,669 B2 | 2/2018 | Touma |
| 10,071,282 B2 | 9/2018 | Deangelis |
| 10,071,301 B2 | 9/2018 | Vock |
| 10,182,135 B2 | 1/2019 | Black |
| 10,292,650 B2 * | 5/2019 | Greenwald ............ A61B 5/002 |
| 2002/0011250 A1 | 1/2002 | Stewart |
| 2002/0024450 A1 | 2/2002 | Townsend |
| 2002/0049507 A1 | 4/2002 | Hameen-Anttila |

(56) References Cited

U.S. PATENT DOCUMENTS

| | | |
|---|---|---|
| 2002/0060633 A1 | 5/2002 | Crisco |
| 2002/0087054 A1 | 7/2002 | Lin |
| 2002/0116147 A1 | 8/2002 | Vock |
| 2002/0183657 A1 | 12/2002 | Socci |
| 2003/0014210 A1 | 1/2003 | Vock |
| 2003/0071766 A1 | 4/2003 | Hartwell |
| 2003/0151554 A1 | 8/2003 | McCarthy |
| 2003/0163287 A1 | 8/2003 | Vock |
| 2003/0217582 A1 | 11/2003 | Reinbold |
| 2004/0008106 A1 | 1/2004 | Konczal |
| 2004/0225236 A1 | 11/2004 | Wheeler |
| 2004/0240198 A1 | 12/2004 | Laar |
| 2005/0177929 A1 | 8/2005 | Greenwald |
| 2006/0038694 A1 | 2/2006 | Naunheim |
| 2006/0074338 A1 | 4/2006 | Greenwald |
| 2007/0061106 A1 | 3/2007 | Vock |
| 2010/0076321 A1 | 3/2010 | Zhang |
| 2010/0076692 A1 | 3/2010 | Vock |
| 2011/0215931 A1 | 9/2011 | Callsen |
| 2012/0210498 A1 | 8/2012 | Mack |
| 2012/0220893 A1 | 8/2012 | Benzel |
| 2013/0060168 A1 | 3/2013 | Chu |
| 2013/0074248 A1 | 3/2013 | Evans |
| 2013/0110415 A1 | 5/2013 | Davis |
| 2014/0288432 A1 | 9/2014 | Hennig |
| 2014/0364772 A1 | 12/2014 | Howard |
| 2015/0250250 A1 | 9/2015 | Ellis |
| 2017/0300755 A1 | 10/2017 | Bose |

FOREIGN PATENT DOCUMENTS

| | | |
|---|---|---|
| WO | 9836213 | 8/1998 |
| WO | 9904685 | 2/1999 |
| WO | 02053024 | 7/2002 |
| WO | 2006036567 | 4/2006 |

OTHER PUBLICATIONS

Greenwald, Richard M., Head Impact Severity Measures for Evaluating Mild Traumatic Brain Injury Risk Exposure, Apr. 2008, Neurosurgery, 62(4), pp. 789-798.

Duma, Stefan M., Analysis of Real-time Head Accelerations in Collegiate Football Players, Jan. 2005, Clin J Sport Med, vol. 15, No. 1, pp. 3-8.

Declaration from Nelson Kraemer regarding the discovery of the Radio Telemetry Project materials, Dec. 5, 2017 (2 pages).

Report No. 1062—Radio Telemetry Project, Progress Report No. 1, Jun. 9, 1964 (253 pages).

Report No. 1062—Radio Telemetry Project, Appendix A-C, Apr. 1963 (115 pages).

Report No. 1062—Radio Telemetry Project, Appendix D, Book 1, 1964 (108 pages).

Report No. 1062—Radio Telemetry Project, Appendix D, 1963 (159 pages).

Radio Telemetry Project Test Data, Aug. 25, 1964 (24 pages).

Radio Station License for Radio Telemetry Project, Jul. 7, 1965 (2 pages).

Operating Instructions for Radio Telemetry System, Apr. 1967 (10 pages).

Various Photographs related to Radio Telemetry Project, Oct. 1966 (84 pages).

Bai et al., A Portable ECG and Blood Pressure Telemonitoring System, Jul./Aug. 1999, IEEE Engineering in Medicine and Biology, pp. 63-70.

Coleman et al., Ambient Head Temperature and Football Helmet Design, Mar. 1972, Medicine, Science, Exercise and Sports Journal, 19 pages.

Foxlin et al., Miniature 6-DOF Inertial System for tracking HMDs, Apr. 13-14, 1998, SPIE, Helmet and Head-Mounted Displays III, AeroSense 98, vol. 3362.

Gibilisco, "Encode." The Illustrated Dictionary of Electronics. McGraw-Hill. 2001. Eighth edition. p. 257.

International Search Report for PCT/US2005/032903 dated Mar. 10, 2006.

Written Opinion for PCT/US2006/000536 dated Jul. 10, 2007.

International Search Report for PCT/US2006/000536 dated Oct. 2, 2006.

King, A. I. et al., "Mechanics of the Head/Neck." The Biomedical Engineering Handbook: Second Edition. Dec. 28, 1999. CRC Press LLC. pp. 23-1:23-12.

Medendorp et al., Off-centric Rotation Axes in Natural Head Movements: Implications for Vestibular Reafference and Kinematic Redundancy, The American Physiological Society, 1998, pp. 2025-2039.

Merono et al., Movement Evaluator System Via R.F. Transmission, 1995 IEEE, pp. 94-97.

Moon, Donald W., et al., "Peak Head Acceleration of Athletes During Competition-Football," Medicine and Science in Sports, Spring 1971, vol. 3, No. 1, pp. 44-50.

Naunheim, Rosanne S., et al. "Comparison of impact data in hockey, football, and soccer." Journal of Trauma and Acute Care Surgery 48.5 (2000): 938-941.

Padgaonkar, A.J. et al., "Measurement of Angular Acceleration of a Rigid Body Using Linear Accelerometers," Journal of Applied Mechanics, Sep. 1975, pp. 552-556.

Puers et al., A Telemetry System for the Detection of Hip Prosthesis Loosening by Vibration Analysis, Aug. 25, 2000, Sensors and Actuators, vol. 85, pp. 42-47.

Reid et al., Head Protection in Football, Sports Medicine, Mar./Apr. 1974, pp. 86-92.

Schatz, P., et al., "Computer-Based Assessment of Sports-Related Concussion", Applied Neuropsychology, 2003, vol. 10, No. 1, pp. 42-47.

International Search Report and Written Opinion issued in PCT/US2019/066084 dated Mar. 9, 2020 (13 pages).

* cited by examiner

SYSTEM FOR MONITORING A PHYSIOLOGICAL PARAMETER OF PLAYERS ENGAGED IN A SPORTING ACTIVITY

CROSS-REFERENCE TO RELATED APPLICATIONS

This application is a continuation of U.S. patent application Ser. No. 14/450,928, filed Aug. 4, 2014, which is a continuation of U.S. patent application Ser. No. 11/225,880, filed Sep. 13, 2005, which claims priority from U.S. Provisional Patent Application No. 60/609,555, filed Sep. 13, 2004, all of which are incorporated herein by referenced and made a part hereof.

FEDERALLY SPONSORED RESEARCH OR DEVELOPMENT

A portion of the invention described herein was made in the course of work under grant number 1R43HD4074301 from the National Institute of Health. The U.S. Government may retain certain rights in this invention.

TECHNICAL FIELD

The invention relates to a multi-component system that actively monitors a physiological parameter of numerous players engaged in a sporting activity. The system includes reporting units that provide for the transmission of each player's measured physiological data to a controller for calculation of the parameter and recordation of the results. Since most contact sports involve multi-player teams, the system can simultaneously measure, record and transmit data on the physiological parameter(s) for all players on the team throughout the course of play, including a game or practice.

BACKGROUND OF THE INVENTION

Due to the physical nature of contact sports, such as football, hockey, and lacrosse, players receive a number of impacts during the course of play. The impacts cause an acceleration of the player's body part, including the head and brain.

Much remains unknown about the response of the brain to head accelerations in the linear and rotational directions and even less about the correspondence between specific impact forces and injury, particularly with respect to injuries caused by repeated exposure to impact forces of a lower level than those that result in a catastrophic injury or fatality. Almost all of what is known is derived from animal studies, studies of cadavers under specific directional and predictable forces (i.e. a head-on collision test), from crash dummies, from human volunteers in well-defined but limited impact exposures, or from other simplistic mechanical models. The conventional application of known forces and/or measurement of forces applied to animals, cadavers, crash dummies, and human volunteers limits our knowledge of a relationship between forces applied to a living human head and resultant severe and catastrophic brain injury. These prior studies have limited value as they typically relate to research in the automobile safety area.

The concern for sports-related injuries, particularly to the head, is higher than ever. The Center for Disease Control and Prevention estimates that the incidence of sports-related mild traumatic brain injury (MTBI) approaches 300,000 annually in the United States. Approximately ⅓ of these injuries occur in football. MTBI is a major source of lost player time. Head injuries accounted for 13.3% of all football injuries to boys and 4.4% of all soccer injuries to both boys and girls in a large study of high school sports injuries. Approximately 62,800 MTBI cases occur annually among high school varsity athletes, with football accounting for about 63% of cases. Concussions in hockey affect 10% of the athletes and make up 12%-14% of all injuries.

For example, a typical range of 4-6 concussions per year in a football team of 90 players (7%), and 6 per year from a hockey team with 28 players (21%) is not uncommon. In rugby, concussion can affect as many as 40% of players on a team each year. Concussions, particularly when repeated multiple times, significantly threaten the long-term health of the athlete. The health care costs associated with MTBI in sports are estimated to be in the hundreds of millions of dollars annually. The National Center for Injury Prevention and Control considers sports-related traumatic brain injury (mild and severe) an important public health problem because of the high incidence of these injuries, the relative youth of those being injured with possible long term disability, and the danger of cumulative effects from repeat incidences.

Athletes who suffer head impacts during a practice or game situation often find it difficult to assess the severity of the blow. Physicians, trainers, and coaches utilize standard neurological examinations and cognitive questioning to determine the relative severity of the impact and its effect on the athlete. Return to play decisions can be strongly influenced by parents and coaches who want a star player back on the field. Subsequent impacts following an initial concussion (MTBI) may be 4-6 times more likely to result in a second, often more severe, brain injury. Significant advances in the diagnosis, categorization, and post-injury management of concussions have led to the development of standardized tools such as the Standardized Assessment of Concussion (SAC), which includes guidelines for on-field assessment and return to sport criteria. Yet there are no objective biomechanical measures directly related to the impact used for diagnostic purposes. Critical clinical decisions are often made on the field immediately following the impact event, including whether an athlete can continue playing. Data from the actual event would provide additional objective data to augment psychometric measures currently used by the on-site medical practitioner.

Brain injury following impact occurs at the tissue and cellular level, and is both complex and not fully understood. Increased brain tissue strain, pressure waves, and pressure gradients within the skull have been linked with specific brain injury mechanisms. Linear and rotational head acceleration are input conditions during an impact. Both direct and inertial (i.e. whiplash) loading of the head result in linear and rotational head acceleration. Head acceleration induces strain patterns in brain tissue, which may cause injury. There is significant controversy regarding what biomechanical information is required to predict the likelihood and severity of MTBI. Direct measurement of brain dynamics during impact is extremely difficult in humans.

Head acceleration, on the other hand, can be more readily measured; its relationship to severe brain injury has been postulated and tested for more than 50 years. Both linear and rotational acceleration of the head play an important role in producing diffuse injuries to the brain. The relative contributions of these accelerations to specific injury mechanisms have not been conclusively established. The numerous mechanisms theorized to result in brain injury have been evaluated in cadaveric and animal models, surrogate models, and computer models. Prospective clinical studies combining head impact biomechanics and clinical outcomes have been strongly urged. Validation of the various hypotheses and models linking tissue and cellular level parameters with MTBI in sports requires field data that directly correlates specific kinematic inputs with post-impact trauma in humans.

In the prior art, conventional devices have employed testing approaches which do not relate to devices which can be worn by living human beings, such as the use of dummies. When studying impact with dummies, they are typically secured to sleds with a known acceleration and impact velocity. The dummy head then impacts with a target, and the accelerations experienced by the head are recorded. Impact studies using cadavers are performed for determining the impact forces and pressures which cause skull fractures and catastrophic brain injury.

There is a critical lack of information about what motions and impact forces lead to MTBI in sports. Previous research on football helmet impacts in actual game situations yielded helmet impact magnitudes as high as 530 G's for a duration of 60 msec and >1000 G's for unknown durations with no known MTBI. Accelerometers were held firmly to the head via the suspension mechanism in the helmet and with Velcro straps. A recent study found maximum helmet accelerations of 120 G's and 150 G's in a football player and hockey player, respectively. The disparity in maximum values among these limited data sets demonstrates the need for additional large-scale data collection.

Most prior art attempts relate to testing in a lab environment. However, the playing field is a more appropriate testing environment for accumulating data regarding impact to the head. A limitation of the prior art involves practical application and widespread use of measurement technologies that are size and cost effective for individuals and teams. Therefore, there would be significant advantage to outfitting an entire playing team with a recording system for monitoring impact activities. This would assist in accumulating data of all impacts to the head, independent of severity level, to study the overall profile of head impacts for a given sport. Also, full-time head acceleration monitoring would also be of great assistance in understanding a particular impact or sequence of impacts to a player's head over time that may have caused an injury and to better treat that injury medically.

The present invention is provided to solve the problems discussed above and other problems, and to provide advantages and aspects not provided by prior systems of this type. A full discussion of the features and advantages of the present invention is deferred to the following detailed description, which proceeds with reference to the accompanying drawings.

SUMMARY OF THE INVENTION

The present invention provides a multi-component system that actively monitors at least one physiological parameter of players engaged in a sporting activity. The system includes reporting units with a telemetry element that provide for the transmission of each player's physiological parameter data to a controller for calculation, recordation and/or storage. The reporting unit can be installed with each player's protective equipment. Since most contact sports involve multi-player teams, the system simultaneously measures, records and transmits the data on the physiological parameter(s) for all players on the team having a reporting unit throughout the course of play, including a game or practice. The system is especially well suited for helmeted team sports where players are susceptible to head impacts and injuries; for example, football, hockey, and lacrosse. Since the system can be employed with every member of the team, the system simultaneously measures, transmits and/or records impact physiological data from each player throughout the course of the practice or game.

According to an aspect of the present invention, the system actively measures and calculates the acceleration of a body part (e.g. the head) of players while engaged in physical activity, such as during play of a contact sport. When the calculated body part acceleration exceeds a predetermined level, a system controller transmits a signal to a signaling device to notify sideline personnel that a player(s) has experienced an elevated body part acceleration. To assist with future monitoring and evaluation, a system database stores the calculated body part acceleration for each player.

According to another aspect of the present invention, the system actively measures and calculates each player's body surface temperature during play. When the calculated body temperature exceeds a predetermined level, the system controller transmits a signal to the signaling device to notify sideline personnel that a player(s) has experienced a significant body temperature increase.

According to yet another aspect of the invention, the system actively measures and calculates the acceleration of each player's body part and the player's temperature during play. Thus, the system can actively monitor multiple physiological parameters for each of the many players engaged in physical activity.

Other features and advantages of the invention will be apparent from the following specification taken in conjunction with the following drawings.

BRIEF DESCRIPTION OF THE FIGURES

To understand the present invention, it will now be described by way of example, with reference to the accompanying figures in which.

DETAILED DESCRIPTION

Figure 1:
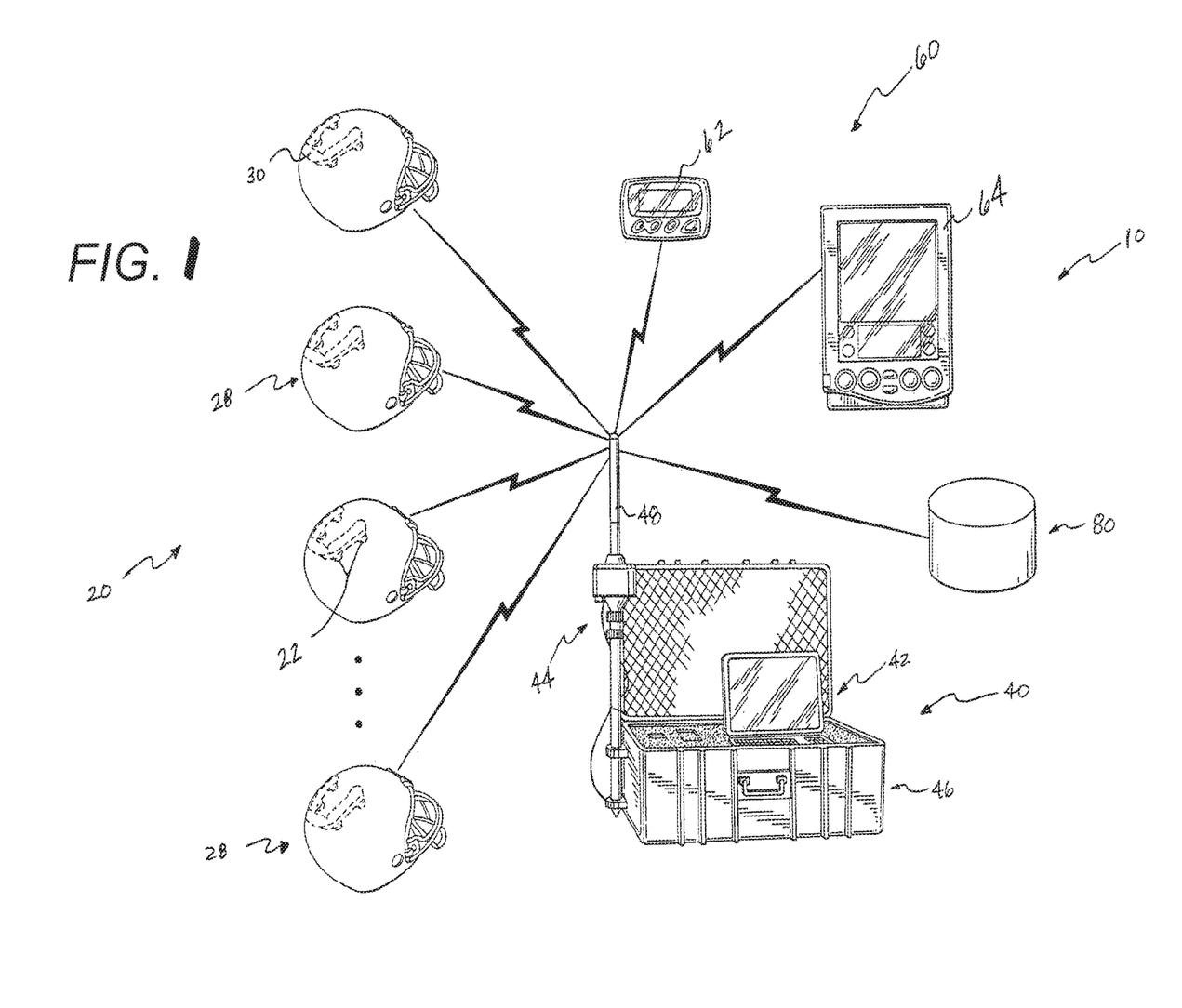
FIG. 1 is a perspective view of the system of the invention, showing the system configured for use with football helmets.
Figure 2:
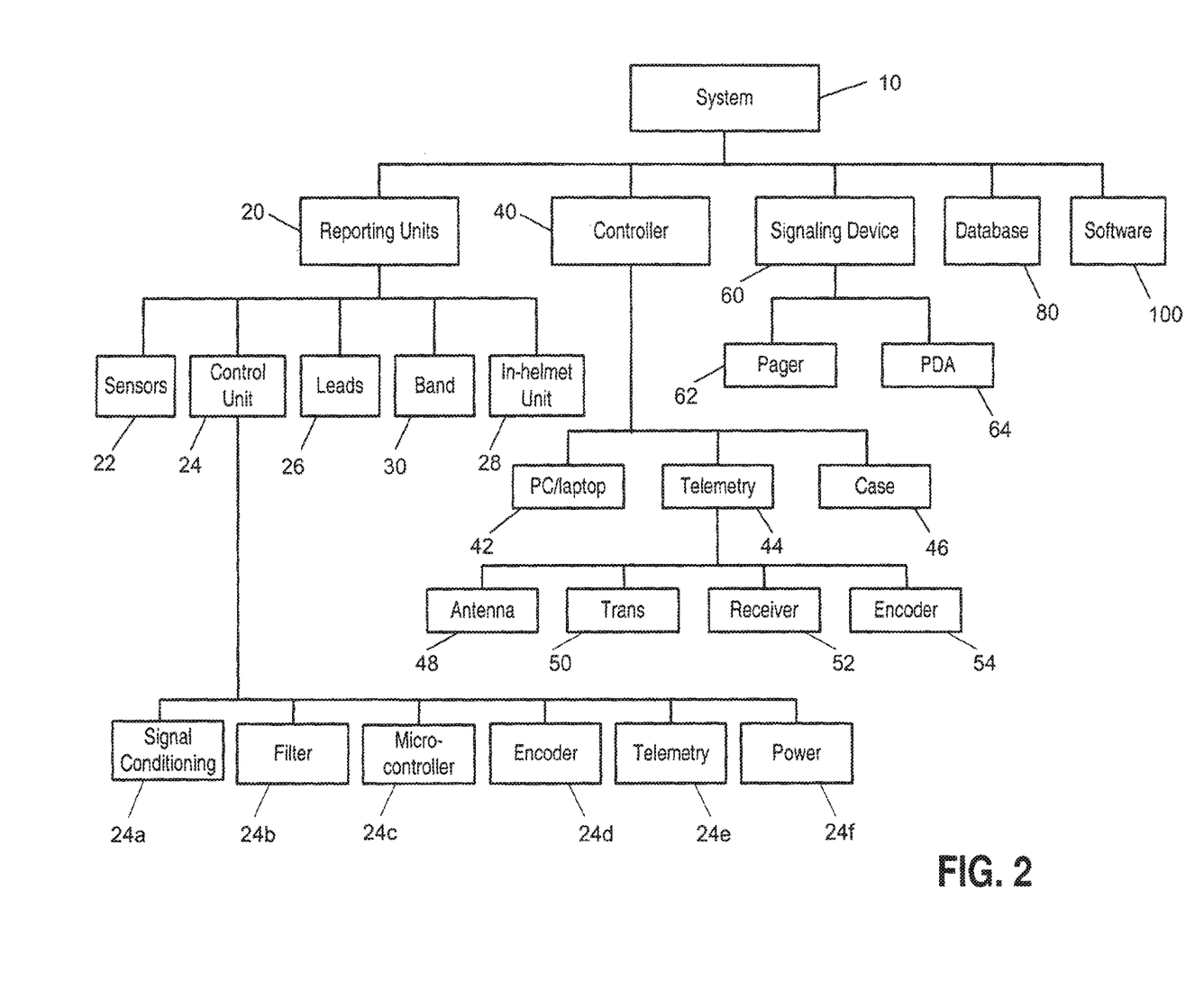
FIG. 2 is a block diagram of the system of the invention.

FIGS. 1 and 2, depict a multi-component system 10 for actively monitoring a physiological parameter of numerous players engaged in a sporting activity, wherein the players' data is transmitted to a controller for monitoring and recordation. In one embodiment, the system 10 is configured to measure and calculate the acceleration of a body part (e.g., the head) of players while engaged in physical activity, such as during play of a contact sport. In another embodiment, the system 10 is designed to measure and calculate each player's body temperature during play. In yet another embodiment, the system 10 is designed to measure and calculate the acceleration of each player's body part and the player's temperature during play. Since most contact sports involve multi-player teams, the system 10 simultaneously measures, records and transmits the data on the physiological parameter(s) for all players on the team throughout the course of play, including a game or practice. The system 10 is especially well suited for helmeted team sports where players are susceptible to head impacts and injuries; for example, football, hockey, and lacrosse. Therefore, the system 10 represents a platform for actively monitoring the physiological parameters of players engaged in sporting activities. It is within the scope of the invention for the system 10 to be configured to monitor a physiological parameter of a smaller number of players, meaning not all players engaged in the physical activity.

The system 10 is generally comprised of multiple reporting units 20, a controller unit 40, a signaling device 60, a database 80, and software 90 that enables the various components of the system 10 to communicate and interact. While the system 10 is described below in the context of a helmeted team sport, the system 10 can be utilized in connection with other sporting activities that do not require a helmet, such as soccer or rugby. Consequently, the system 10 can be configured for use with other protective gear, such as a head band, leg guard, or shoulder pad. Because a football team includes numerous players, in some cases exceeding one hundred players, each player has a recording unit 20 that communicates with the controller 40. Therefore, the recording units 20 continuously and collectively measure and transmit physiological data to the controller for monitoring of the players. While a significant portion of the parameter measurement and monitoring occurs during the course of play, the system 10 continues to measure relevant physiological parameters, such as the players' body temperature, when players are at a reduced activity level on the sideline.

Figure 3:
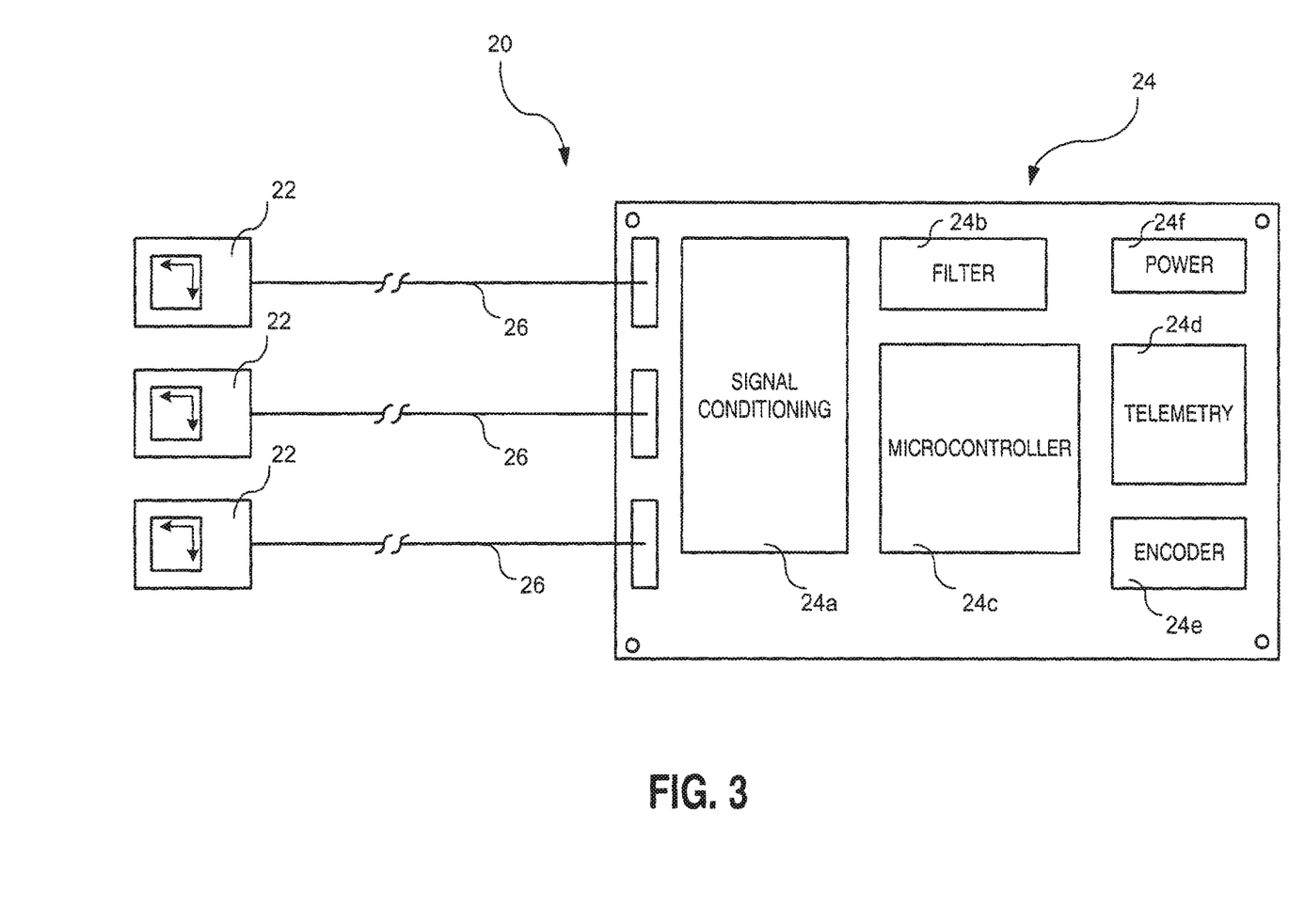
FIG. 3 is a schematic of a reporter unit of the system of the invention.

The reporting unit 20 automatically and continuously measures and records the player's physiological parameters and transmits data regarding the parameter to the controller 40. When the system 10 is configured for use with a football team, the wearable reporting unit 20 is adapted for use either within each player's helmet or protective gear, such as shoulder pads. Referring to FIGS. 1-4 and as explained in co-pending U.S. patent application Ser. No. 10/997,832 which is incorporated herein by reference, the reporting unit 20 includes a sensor assembly defined by a plurality of sensors 22 that measures the player's physiological parameter and a control unit 24, wherein the sensors 22 are operably connected to the control unit 24. As shown in FIG. 3, a wire lead 26 electrically connects each sensor 22 with the control unit 24. The control unit 24 can include a signal conditioner 24a, a filter 24b, a microcontroller 24c (or microprocessor), a telemetry element 24d, an encoder 24e, and a power source 24f. While the encoder 24e is shown as separate from the telemetry element 24d, the encoder 24e can be integrated within the telemetry element 24d. The sensors 22 are calibrated to measure the player's physiological condition or parameter and then generate input data regarding each parameter. The control unit 24 processes the input data, including filtering and conditioning as necessary, and then converts the data to signals. Next, the encoder 24e of the control unit 24 encodes the signals with a unique identifier, and the telemetry element 24d wirelessly transmits (as represented by the lightening bolts in FIG. 1) the encoded signals to the remote controller 40 which recognizes the encoded signals for further processing and calculation. The telemetry element 24d can be a transceiver, or a separate receiver and transmitter. The power source 24f can be a rechargeable battery or a disposable battery. In another embodiment of the system 10, the parameter data transmitted from the reporters 20 to the controller 40 can be encrypted to increase the security of the underlying data. In this configuration, the system 10 can include a cipher for performing encryption and decryption, and a key to parameterize the cipher.

The type of sensors 22 within the reporting unit 20 depend upon the player's physiological data to be measured, transmitted and monitored. For example, when the reporting unit 20 is configured to measure acceleration of the body part, the sensors 22 are single-axis accelerometers, multi-axis accelerometers, or a combination of both. As another example, to measure the player's temperature, each reporting unit 20 includes at least one sensor 22 such as a thermistor, which comprises resistive circuit components having a high negative temperature coefficient of resistance so that the resistance decreases as the temperature increases. Alternatively, the temperature sensor 22 is a thermal ribbon sensor or a band-gap type integrated circuit sensor. To measure both the acceleration and temperature of the player's body part, the sensors 22 can be a combination of accelerometers and thermistors operably connected to the control unit 24. Where the system 10 is configured for use with a football team to measure and monitor head acceleration and player body temperature, the sensors 22 are accelerometers and thermistors that are arrayed in an in-helmet unit 28 (see FIG. 4) for each player. To measure other physiological parameters, such as the player's heart rate and blood pressure the sensors 22 are micro electro-mechanical system (MEMS) type sensors that use auscultatory and/or oscillometric measurement techniques.

Figure 4:
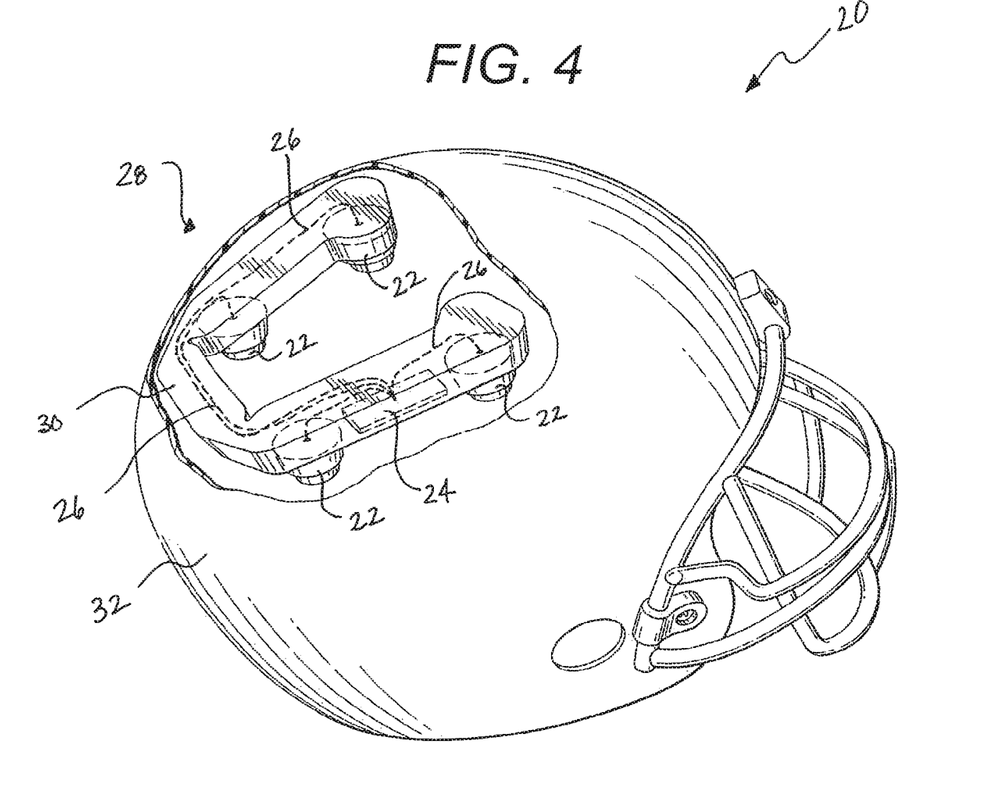
FIG. 4 is a perspective view of a reporting unit of the system of the invention, showing an in-helmet version of the reporting unit.

As shown in FIG. 4, the in-helmet unit 28 includes a flexible band 30 that houses the sensors 22 and the control unit 24. The flexible band 30 is received within the internal padding assembly of the helmet 32, wherein the sensors 22 are positioned about the player's skull. In this manner, the in-helmet unit 28 is removably received within the helmet 32 to allow for testing and maintenance, including recharging of the battery power source. In one embodiment where the system 10 measures the acceleration of the player's head, the band 30 is dimensioned such that the sensitive axis of each accelerometer sensor 22 is orthogonal to the outer surface of the player's head. In another embodiment, the accelerometer sensors 22 are not positioned orthogonal to the head surface. Depending upon the other design parameters of the system 10, the accelerometer sensors 22 can be positioned either orthogonally or non-orthogonally to each other. While FIG. 3 depicts three sensors 22 within the control unit 20, the precise number of sensors 22 varies with the design of the system 10. In the embodiment where the system 10 measures the player's temperature, the temperature sensor 22 can be placed within the forehead pad of the helmet 32 or at other locations in protective equipment, such as shoulder pads, knee pads, etc.

In operation, the reporting unit sensors 22 measure the physiological parameter(s) and generate signals in response to the measured parameter value. The sensors 22 can be configured to continuously generate signals in response to the parameter value, or generate signals only when the parameter value reaches or exceeds a threshold level. For example, the sensors 22 can be single-axis accelerometers that measure head acceleration but only generate signals when the sensed head acceleration surpasses 10 G's. The control unit 24 processes the data signals and transmits them to the sideline controller 30 for calculation and monitoring of the player's physiological condition. As part of the processing step, the control unit 24 conditions and filters the signals, as necessary, and then encodes the signals with a unique identifier for transmission to the controller 40. To support simultaneous transmissions from multiple reporters 20 to the correct controller 40, the signals sent from each control unit 24 can be divided with time division multiple access (TDMA), code division multiple access (CDMA), or frequency division multiple access (FDMA) technology. Encoding the signals with a unique identifier enables the controller 40 to properly multiplex and decode information from the various reporters 20 transmitting data. Accordingly, the system 10 simultaneously measures and transmits encoded data from a number of reporters 20 and then the controller 40 catalogs either the encoded data signal for further calculation, or the resultant calculation based upon the relationship between the reporter 20 and the player. Regardless of when the cataloging occurs, the controller 40 organizes each player's calculated parameter result for further analysis and/or monitoring. In one embodiment, an operator of the system 10 defines the relationship or association between the reporter 20 and the player when the player is issued a helmet or protective gear having the reporter 20. With the aid of the signaling device 60, the sideline personnel utilizing the system 10 can then monitor the physiological condition of select players based upon the cataloging of the calculated parameter result.

The active monitoring system 10, including the reporting unit 20, can be configured to measure the severity of the impact upon the player's body part based upon indirect measures of the impact event. This indirect measurement is accomplished through monitoring the deformation experienced by the player's protective gear, including the helmet, the shoulder pads, and the internal padding assembly associated within each. An impact to a body part may be quantified by the body part's impact kinematics, which include a change in position, change in velocity and/or change in acceleration of the part over a select time interval. In one embodiment, small magnetic particles and at least one Hall-effect sensor are embedded within the protective equipment and/or the padding element connected to the equipment. The sensor output is dependent upon the distance between the particles and the sensor, wherein the sensor output measurements are applied to a rheologic model to calculate the impact force experienced by the equipment and/or pad element. For example, a mass-spring-damper model of the padding element and experimentally derived foam displacement and velocity values can be utilized in the model to estimate or calculate the impact acceleration and the magnitude of the applied impact force. A highly sensitive sensor array can be used to calibrate the protective gear or padding element to determine the location of the magnetic particles therein relative to the Hall-effect sensor(s). In another embodiment, the impact to the body part is measured and calculated based upon the change in shape or dimensions of the protective gear and/or the padding element connected thereto. Resistive sensing elements can be used where the resistance in the measurement device changes as a function of linear, torsional or shear displacement. Alternatively, capacitive sensing elements can be utilized where the capacitance changes as a function of linear, torsional or shear displacement. Shape-changing tape is an example of the sensing elements. In another embodiment of system 10, the reporting unit 20 includes a micro electro-mechanical system (MEMS) pressure transducer that detects pressure changes within an enclosed fluid bladder or air chamber, such as those used with the padding assembly of protective sports equipment, such as helmets and shoulder pads. When the protective equipment to which the padding assembly is connected receives an impact force, the padding assembly compresses the fluid causing a pressure change that is measured by the MEMS pressure transducer. Since environmental conditions, including temperature and humidity, affect the fluid bladders and air chambers, the reporting unit 20 includes a temperature compensation element to improve the accuracy of the resulting measurements. In yet another embodiment of the system 10, the reporting unit 20 measures the characteristic sound generated by an impact to a body part and/or the protective equipment overlying the body part. The system 10 employs pattern recognition to provide continuous evaluation of sounds resulting from impacts in order to characterize the severity of the impact on a scale. The software 100 associated with the pattern recognition distinguishes impact-related sounds from ambient sounds typically found at a playing field, or selectively filters the ambient sounds so as to avoid skewing the analysis and results. The system 10 then categorizes the severity of the impact based upon the characteristics of the impact-related sound. One benefit of these approaches is that the system 10 can positively quantify the fit of the protective equipment or padding element with respect to the player, and provide an alert if there is an improper equipment fit.

Generally, the controller 40 receives the data measured and transmitted by the reporting units 20 and processes the data for meaningful analysis or use. The sideline controller 40 is comprised of a portable microprocessor 42 (e.g., a laptop or portable computer), including a display screen, and a telemetry element 44 operably connected to the microprocessor 42. The controller 40 is a mobile apparatus that can be transported in a case 46. Referring to FIG. 2, the telemetry element 44 includes an antenna 48, a transmitter 50, a receiver 52 (or a combined transceiver), and an encoder 54. Consistent with that explained above, the telemetry element 44 decodes the encoded signals sent from each reporter 20, performs the requisite calculation, and then multiplexes the result according to the identity of the reporting unit 20. In this manner, the controller 40 recognizes the identifier provided by each reporter 20 and organizes the results for each player having a reporter 20. The controller 40 has a local memory device for storing data received from the reporting units 20 and the subsequently calculated results. Preferably, the memory device of the controller 40 is capable of storing information compiled over an entire season, so if necessary, sideline personnel and/or medical staff can retrieve historical player data when needed. In preferred embodiments, the controller 40 can be equipped with software 100 that includes team management information (e.g., complete roster list of players, position of players, identification of active players, etc.) and daily exposure information (e.g., date, game vs. practice, conditions, etc.). The controller 40 also is used to synchronize local data (e.g., one team or historical data) with the centralized database 80.

In operation, the controller 40 receives the encoded signal from the reporting unit 20 for the measured physiological parameter (the "measured parameter") and processes the data within the signal to calculate a result for the parameter (the "parameter result"). When the parameter result reaches or exceeds a predetermined parameter level (hereinafter the "alert event"), the controller 40 communicates with the signaling device 60 thereby alerting the sideline personnel bearing the device 60. For each alert event, the controller 40 displays the affected player's identity, for example by name or jersey number, the measured parameter, and the time of the alert event. However, the player's identity can be protected by use of a unique player identifier, which may be encoded or encrypted. When the parameter result falls below the level and an alert event does not occur, the controller 40 continues to receive data from the reporters 20 and runs the requisite calculations. Further, when an alert event arises from one reporter 20, the controller 40 continues to receive and process data from the other reporters 20. The time stamp allows sideline personnel and medical staff to correlate the calculated parameter to actual videotape of the sporting event that led to the alert event. Once an alert event has occurred, the controller 40 sends a signal to the signaling device 60 that alerts the sideline personnel to observe and investigate the condition of the player in question. The player in question is quickly identified by the controller 40 due to the unique identifier provided by the reporting units 20 and the subsequent recognition of the identifier and the multiplexing performed by the controller 40. In this manner, the sideline personnel can efficiently evaluate the player at issue from the many players comprising the team.

As a further aspect of the operation of the system 10, the telemetry element 44 of the controller 40 can transmit a confirmation signal to each reporting unit 20 confirming that the signals sent by that reporting unit 40 were successfully received and that the data is complete for calculation purposes. This enables the reporting units 20 to conserve power since they do not have to repeatedly send data to the controller 40. In the event that the signals from a reporting unit 20 are not successfully received or that the signals are incomplete or skewed, the telemetry element 44 transmits a resend signal that instructs the reporter 20 to resend the signals from the control unit 24 for reception by the controller 40. The reporter 20 can be programmed to automatically resend signals to the controller 40 in the situation where the confirmation signal is not received within a fixed period of time from the signal transmission by the reporter 20. Since numerous reporters 20 are simultaneously transmitting data signals during the course of play, the controller 40 is constantly assessing the quality of the transmitted signal and sending the relevant confirmation and resend signals to the various reporters 20.

In the embodiment where the system 10 measures player body part acceleration, such as head acceleration, when an alert event occurs, the controller 40 calculates the point of impact on the player's body part, the cumulative impacts sustained by the player during the current sporting session, and then graphs the magnitude and duration of recent impacts to the player and/or the body part. As part of this calculation, the controller 40 uses an algorithm to estimate the magnitude of the impact measured by the sensors 22, wherein the algorithm comports with the disclosure of co-pending U.S. patent application Ser. No. 10/997,832. As an example, when the system 10 measures and monitors the player's head acceleration, the controller 40 sends a signal to a signaling device 60 when an impact magnitude exceeding a predetermined threshold level (e.g., 50 G's) is measured and calculated. When this alert event occurs, the controller 40 calculates the point of impact on the player's head, the cumulative impacts sustained by the player during the current sporting session, and then graphs the magnitude and duration of recent head impacts for review by sideline personnel, including the training and medical staff.

In the embodiment where the system 10 monitors each player's body temperature, the controller 40 receives data from the reporting units 20 and then calculates each player's body surface temperature, the rate of temperature increase and/or decrease versus a selected time interval. In addition to the temperature sensor 22 in the reporting unit 20, the controller 40 can include an additional temperature and/or humidity sensor to measure ambient conditions and use the resulting data for correction purposes. When the system 10 is configured for player body temperature monitoring in helmeted team sports, the reporting unit 20 can be positioned within the helmet 32 or within other protective equipment worn by each player, such as a shoulder pad assembly. The controller 40 receives the temperature data from each reporter 20 and then applies an algorithm to calculate the player's body surface temperature, the rate of temperature increase and/or decrease, and other temperature-based parameters that aid in the evaluation of player thermal management.

As explained above, the signaling device 60 communicates with the controller 40 and alerts sideline personnel when a suspect event has occurred. The signaling device 60 can be a pager 62, a personal digital assistant (PDA) 64, or a portable electronic device, such as a telephone, that is capable of receiving data and displaying results transmitted by the controller 40. Typically, the device 60 is worn or held by sideline personnel, including the training staff, medical personnel and/or coaches. Depending upon the parameters of the system 10, the signaling device 60 could vibrate or sound an audio alarm when a suspect event is measured and recorded, and inform the wearer of the device 60 of the alert event. Regarding the nature of the alert event, the device 60 can advise of: the identity of player(s) affected; the nature of the suspect event, including an elevated head acceleration due to impact or a change in a player's physiological status such as elevated body temperature; and the time of the incident.

In one embodiment, the PDA 64 is programmed with software 100 that assures best practices are followed in the treatment and documentation of mild traumatic brain injuries (MTBI). In another embodiment of the present invention, the PDA 64 software 100 includes a bundle of team management programs which enables the PDA 64 to store all team data, including medical histories and testing baselines. The software 100 also provides the PDA 64 with an active response protocol for guiding sideline personnel through appropriate examination procedures and recording the results. For example, when an alert event occurs and the relevant player is brought to the sideline for evaluation, the PDA 64 can display the individual's head-injury history, the results of previous evaluations and other pertinent medical data. With the assistance of the software 100, the PDA 64 prompts the medical staff member to conduct the appropriate sideline examination, records the responses, compares the results to established baselines and prompts either further testing or a play/no-play decision. The software 100 has a bundle of team management tools that includes a roster program which contains all the basic information about each individual player: e.g., contact information, which sports they play (including position and jersey number), emergency information, relevant sizes, equipment issues and availability to play. Information can be stored and sorted in a variety of ways, such as by team, person item and size. The software 100 may also include a session manager program that allows the coaching staff to document incidents as they occur during a practice or a game. The appropriate information about the team, players and Conditions is entered at the beginning of each session. Then, as injuries occur, the software 100 provides a template for recording injury data by player.

In another embodiment of the inventive system 10, the controller 40 is omitted and the reporting units 20 interact and communicate directly with the signaling device 60. In one version of this embodiment, the reporting units 20 measure the physiological parameters as explained above and perform the related calculations within their control unit 24. All of the calculated results are then transmitted from each reporting unit 20 to the signaling device 60, for example the PDA 64, for recordation and monitoring. The device 60 sorts and multiplexes the results while looking for an alert event. When the device 60 finds an alert event, the device 60 alerts the sideline personnel consistent with that explained above. Alternatively, each reporting unit 20 performs the necessary calculations to arrive at a parameter result and then transmits only those results that amount to an alert event. In this manner, the device 60 receives signals from a reduced number of reporters 20 and then alerts sideline personnel accordingly. In another version of this embodiment, the reporting units 20 measure the physiological parameters and transmit the data signals to the device 60, for example the PDA 64, wherein the device 60 performs the related calculations to arrive at the parameter result. When the parameter result amounts to an alert event, the device 60 alerts the sideline personnel to evaluate the player(s) consistent with that explained above. To aid with the analysis of the parameter results and the subsequent player monitoring, the device 60 can be programmed with a bundle of team management software 100 which enable it to store all team data, including medical histories and testing baselines. The device 60 can also be programmed with an active response protocol for guiding sideline personnel through appropriate examination procedures and recording the results. The data and results stored on the device 60 can be uploaded to the database 80 wherein authorized users can access same for team management and player evaluation functions.

Referring to FIGS. 1 and 2, in an embodiment of the present invention, the system 10 includes a server 80, preferably a database server 80. The central database 80 stores data from all remote sites, including information stored on the controller 40 and the signaling device 60. For example, the database 80 can serve as a team administrator database for the athletic department of a large university. That is, an interactive clearinghouse for all athlete information that needs to be shared among various departments or sports. The database 80 is internet enabled to provide remote access to authorized users, including coaches, trainers, equipment managers and administrators, which allows the users to keep abreast of changes in players' status. The database 80 also provides a host of administrative and management tools for team and equipment staff.

To aid with the evaluation and monitoring of the players, the system 10 can be configured to provide indicia of the impact force. Since the system 10 calculates the magnitude, direction and time history of the impact causing the body part acceleration, the system 10 can quantify the severity of the impact on recognized scales, including the head injury criteria (HIC) and the severity index (SI) scales. Combining the data and/or the results into correlative measures may yield new indices that are more sensitive to the alert event. For example, the system 10 can utilize a combination of the measured parameter, the parameter result and/or the alert event to create a risk assessment index (RAI) for each player. The RAI can be used for team management purposes and future monitoring conducted by the system 10, including adjusting the sensitivity and operating parameters of the various components of the system 10. In addition, the system 10 can be configured to provide diagnostic functions from the active monitoring of the players' physiological parameters, including the body part acceleration and body temperature calculations. Essentially, the system 10 can utilize the calculated results to provide diagnostic assistance to the sideline personnel via either the controller 40 or the signaling device 60. As part of the diagnostic assessment, the system 10 weighs a number of factors including the player's medical and injury history, the alert event, and environmental factors.

In another embodiment of the present invention, the system 10 is configured to adjust its monitoring, sensitivity and/or calculations based upon the player's recent medical and injury history. Thus, the operational parameters and standards of the system 10 components, including the reporting units 20, the controller 40 and the signaling device 60, can be adjusted for future monitoring of the players in light of each player's recent data and history. For example, the controller 40 can wirelessly communicate with the reporting unit 20 to adjust the sensitivity of the sensors 22 for an individual player. In this manner, there is a feedback loop between the various components which can increase or decrease the sensitivity of the active monitoring performed by the system 10.

While this invention is susceptible of embodiments in many different forms, there is shown in the drawings and herein described in detail preferred embodiments of the invention with the understanding that the present disclosure is to be considered as an exemplification of the principles of the invention and is not intended to limit the broad aspect of the invention to the embodiments illustrated.

While the specific embodiments have been illustrated and described, numerous modifications come to mind without significantly departing from the spirit of the invention, and the scope of protection is only limited by the scope of the accompanying Claims.

The invention claimed is:

1. A system for monitoring and analyzing impacts experienced by a player when engaged in a contact sport, the system comprising:
 a reporting unit positioned within a piece of protective sports equipment that is worn against a body part of a player while engaged in a contact sport, the reporting unit having:
  (i) a plurality of sensors arranged against the player's body part to measure impact data resulting from an impact received by the player,
  (ii) a control unit configured to determine impact information from said impact data, and
  (iii) a telemetry element;
 a remote handheld signaling device that receives impact information transmitted from the telemetry element of the reporting unit, the remote handheld signaling device being worn or held by a person not engaged in the play of the contact sport, and the remote handheld signaling device configured to:
  (i) transmit said impact information to a server, and
  (ii) display an alert when a value contained within the impact information is greater than a predetermined alert value;
 the server configured to receive and store said impact information that has been transmitted by the remote signaling device; and
 a computer capable of connecting to the server through the internet, said computer configured to display impact information stored on the server and related to the impact received by the player.

2. The system of claim 1, wherein displayed impact information includes: (i) identification of the player that experienced said impact, (ii) a magnitude of said impact, (iii) a location of said impact, and (iv) a time of said impact.

3. The system of claim 1, wherein the telemetry element is configured to only transmit impact information to a remote handheld signaling device when the value contained within the impact information is greater than the predetermined alert value.

4. The system of claim 1, wherein the impact information includes: (i) a magnitude of said impact received by the player, and (ii) a time of said impact received by the player.

5. The system of claim 4, wherein the telemetry element is configured to only transmit impact information to a remote handheld signaling device when the magnitude of said impact is greater than a predetermined impact magnitude threshold.

6. The system of claim 1, wherein the display of the alert includes showing: (i) the time that the alert occurred, (ii) identification of the player that experienced the impact that resulted in the alert, and (iii) magnitude of the impact that resulted in the alert.

7. The system of claim 1, wherein the protective sports equipment is a helmet, and wherein the plurality of sensing devices are accelerometers configured to be arranged within the helmet proximate the player's head.

8. The system of claim 1, wherein the computer is configured to display a point of impact for said impact that is contained within the impact information.

9. The system of claim 8, wherein the computer is configured to display a direction of impact for said impact that is contained within the impact information.

10. The system of claim 1, wherein the computer is configured to display videotape of the contact sport that is correlated with each impact contained within the impact information stored by the server.

11. The system of claim 1, further comprising a calendar manager configured to schedule two or more of the following activities: (i) games, (ii) practices, (iii) other training sessions, or (iv) injury follow-ups.

12. The system of claim 1, further comprising a roster manager configured to contain information about each player, said information includes at least two of the following: (i) contact information, (ii) position, (iii) jersey number, (iv) equipment sizes, (v) availability to play.

13. The system of claim 1, wherein the predetermined alert value is altered based upon information relating to: (i) the player's medical history or (ii) the player's impact history.

14. A method for monitoring and analyzing impacts experienced by a player when engaged in playing a sport, the method comprising:
providing a reporting unit positioned against a body part of the player while engaged in playing a sport, the reporting unit having: (i) a plurality of sensors, (ii) a control unit, and (iii) a telemetry element;
using at least one sensor of the plurality of sensors to record impact data from an impact experienced by the player;
using the control unit to determine impact information from the impact data, said impact information that includes a magnitude of the impact;
transmitting the impact information to a remote device, if a value contained within the impact information is over a predetermined value;
transmitting the impact information to a server;
accessing the impact information stored on the server using a computer; and
displaying on the computer the identification of the player that experienced the impact and the magnitude of the impact from the accessed impact information.

15. The method of claim 14, wherein the impact information further includes: (i) a location of said impact, (ii) a time of said impact and (iii) a duration of said impact.

16. The method of claim 15, further comprising displaying a direction of said impact contained within the impact information stored on the computer.

17. The system of claim 14, wherein the telemetry element is configured to only transmit impact information to a remote handheld signaling device when an alert value contained within the impact information is greater than a predetermined alert value.

18. The method of claim 17, further comprising displaying an alert on the remote device when the alert value contained within the impact information is over the alert predetermined value.

19. The method of claim 17, wherein displaying the alert includes displaying: (i) identification of the player that experienced said impact, (ii) an magnitude of said impact, (iii) a location of said impact, and (iv) a time of said impact.

20. The method of claim 14, further comprising displaying video of said impact contained within the impact information stored on the computer.

21. The method of claim 14, further comprising using the computer to schedule two or more of the following activities: (i) games, (ii) practices, (iii) other training sessions, or (iv) injury follow-ups.

22. The method of claim 14, further comprising using the computer to enter player information, said information includes at least two of the following: (i) contact information, (ii) position, (iii) jersey number, (iv) equipment sizes, (v) availability to play.

* * * * *